(12) United States Patent
Kam et al.

(10) Patent No.: US 9,498,545 B1
(45) Date of Patent: Nov. 22, 2016

(54) ENVIRONMENTALLY RESPONSIVE HYDROGELS FOR DELIVERY

(71) Applicant: Verily Life Sciences LLC, Mountain View, CA (US)

(72) Inventors: Kimberly Kam, Mountain View, CA (US); Jerrod Joseph Schwartz, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/585,449

(22) Filed: Dec. 30, 2014

Related U.S. Application Data

(60) Provisional application No. 62/068,255, filed on Oct. 24, 2014.

(51) Int. Cl.
*A61K 49/00* (2006.01)

(52) U.S. Cl.
CPC ....... *A61K 49/0006* (2013.01); *A61K 49/0017* (2013.01); *A61K 49/0054* (2013.01)

(58) Field of Classification Search
CPC ................................................ A61K 49/0006
See application file for complete search history.

(56) References Cited

U.S. PATENT DOCUMENTS

| 8,507,283 | B2 | 8/2013 | Stayton et al. | |
|---|---|---|---|---|
| 2010/0254900 | A1* | 10/2010 | Campbell | A61L 27/18 424/1.65 |
| 2011/0266492 | A1 | 11/2011 | Stayton | |
| 2012/0078068 | A1* | 3/2012 | Ulmer | A61B 5/0031 600/302 |
| 2012/0231072 | A1 | 9/2012 | Kang-Mieler | |
| 2013/0171197 | A1* | 7/2013 | Ho | C12N 5/0068 424/400 |

FOREIGN PATENT DOCUMENTS

WO 2015075442 A1 5/2015

OTHER PUBLICATIONS

Lutz, Point by ponit comparison of Two Thermosensitive Polymers Exhibiting a Similar LSCT: Is the AGe of Poly(NIPAM) Over?, J. Am. Chem. Soc, 2006, 128, 13046-13047.*

* cited by examiner

*Primary Examiner* — Paul Dickinson
(74) *Attorney, Agent, or Firm* — McDonnell Boehnen Hulbert & Berghoff

(57) ABSTRACT

A nanosensor-containing polymer composition for the monitoring of physiological parameters and a method for making the composition are disclosed. The composition includes a fluid nanosensor-containing polymer that becomes rigid in the presence of physiological conditions. In the fluid form, the composition can be suitable for injection on to or into the skin. In the rigid form, the nanosensor is substantially immobilized in the polymer. The method includes forming a mixture comprising a nanosensor and polymer precursor(s), subjecting the mixture to conditions suitable for forming the fluid form of the composition; and subjecting the fluid form to physiological conditions to provide a rigid nanosensor-containing composition.

11 Claims, 1 Drawing Sheet

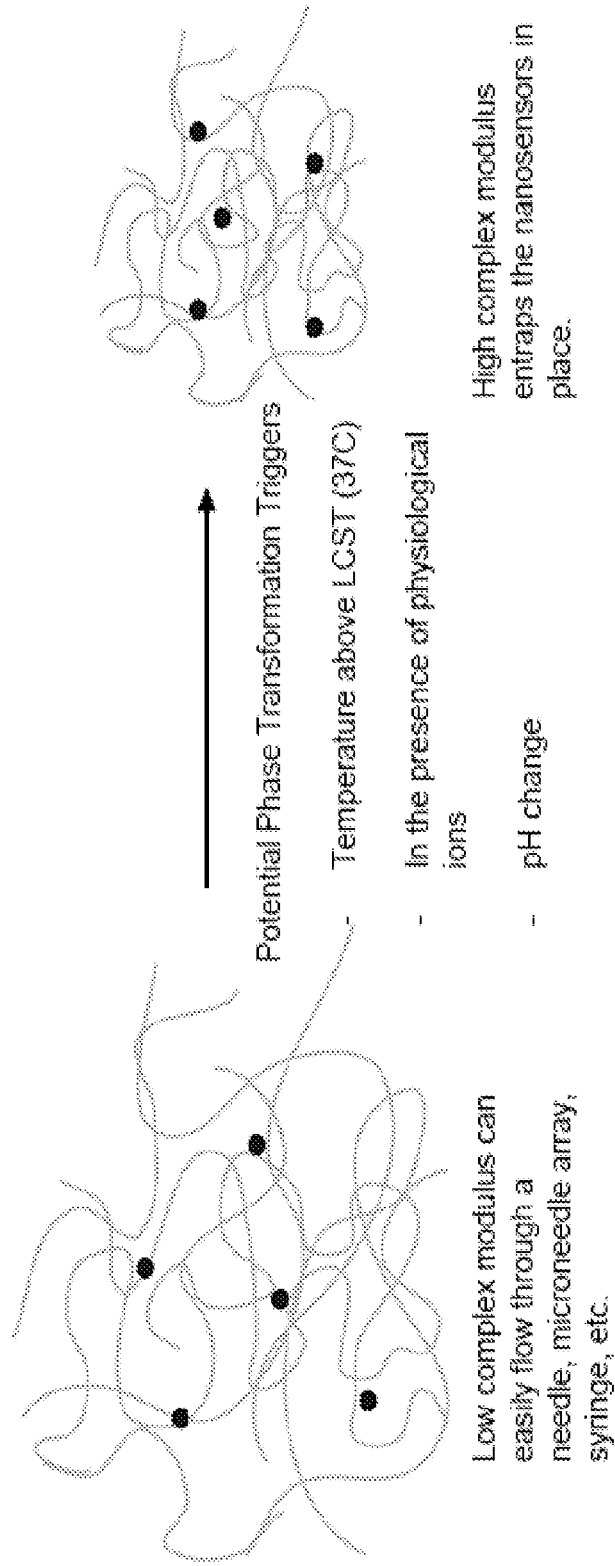

ENVIRONMENTALLY RESPONSIVE HYDROGELS FOR DELIVERY

CROSS-REFERENCE TO RELATED APPLICATION

The present disclosure claims priority to U.S. Provisional Application No. 62/068,255, filed on Oct. 24, 2014, the entire contents of which are herein incorporated by reference.

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a person's blood. The presence or absence of a physiologically relevant analyte in the blood, or the presence at a particular concentration or range of concentrations, may be indicative of a medical condition or the person's state of health. Physiologically relevant analytes may include enzymes, hormones, proteins, cells or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified for some time after the blood work is performed. Thus, the continuous or semi-continuous monitoring of analyte levels is desirable.

Physiologically relevant analytes may also be present in a person's sweat and/or interstitial fluid. These analytes include sugars, salts, fatty acids, amino acids, coenzymes, hormones, neurotransmitters, and cell waste products. The use of analyte sensors on or in the skin are desirable, but are hindered by diffusion of the sensors from the introduction site.

SUMMARY

In one aspect, a composition is disclosed. The composition includes a nanosensor and a polymer that changes from a fluid form to a rigid form in response to a temperature increase or crosslinking.

In another aspect, a method is disclosed. The method involves forming a mixture including a nanosensor a first monomer, a second monomer and an initiator, subjecting the mixture to conditions suitable for copolymerizing the first monomer and second monomer to provide a nanosensor-containing copolymer in a fluid form; and subjecting the resulting fluid copolymer to a temperature above its lower critical solution temperature to provide a rigid nanosensor-containing copolymer.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a diagram of a nanosensor-containing polymer, in accordance with an example embodiment.

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, a composition is disclosed. The composition includes:

a nanosensor including a nanoparticle having a detectable label, where the nanosensor is configured to interact with a specific analyte in an intradermal environment; and a polymer, where the polymer is configured to change from a fluid form to a rigid form in response to a temperature increase;

where the nanosensor is disposed in the polymer.

In another aspect, the composition includes:

a nanosensor including a nanoparticle having a detectable label, where the nanosensor is configured to interact with a specific analyte in an intradermal environment; and a polymer, where the polymer is configured to change from a fluid form to a rigid form in response to crosslinking;

where the nanosensor is disposed in the polymer.

In some embodiments, the nanosensor may comprise a nanoparticle that is functionalized to detect a specific physiologic analyte. For example, the nanoparticle may detect $Na^+$, $K^+$, $Ca^{2+}$, glucose, urea, creatinine, bicarbonate or chloride. The nanoparticle may have a detectable label capable of indicating the interaction of the nanoparticle with an analyte. For example, the nanoparticle may have a fluorophore (i.e., fluorescent label) that changes fluorescence when the nanoparticle interacts with an analyte. The fluorophore could be a pH-sensitive fluorophore that changes its fluorescence properties in response to changes in local pH. The pH-sensitive fluorophore may work in conjunction with an ionophore, which could be in either the nanosensor or the surrounding polymer. The ionophore may interact with a specific ion, such as $Na^+$, $K^+$, or $Ca^{2+}$. The interaction may displace a proton, which, in turn, causes a change in local pH that is indicated by the pH-sensitive fluorophore.

In some embodiments, the polymer is a configured to change from a fluid form to a rigid form in response to one or more physiological conditions. In the fluid form, the polymer may have a viscosity that allows for the polymer to be handled and manipulated as a fluid. In some embodiments, the polymer is capable of being dispensed by a syringe or microneedle. See FIG. 1.

In some embodiments, the change from a fluid form to a rigid form may be in response to a temperature increase. Subjecting a fluid polymer to a temperature above its lower critical solution temperature may provide a rigid form of the polymer. In some embodiments, the temperature increase may be achieved by transdermal application into the intradermal environment.

In other embodiments, the change from a fluid form to a rigid form may be in response to crosslinking. Subjecting a fluid polymer to conditions suitable for initiating crosslinking may provide a rigid form of the polymer. In some embodiments, the composition may include a crosslinking agent. Crosslinking conditions may be selected based on the characteristics and/or relativity of the polymer and, when present, the crosslinking agent. In some embodiments, the temperature increase may be initiated by a component in the intradermal environment. For example, when the polymer is alginic acid, the component may be $Ca^{2+}$.

The nanosensor can be disposed in the polymer in the fluid form so as to be dispensed along with the polymer. For example, the polymer in the fluid form and containing the nanosensor could be introduced into a physiological environment, such as an intradermal environment (i.e., within or proximate to the dermis). Introduction into the intradermal environment could involve transdermal application of the polymer in the fluid form and containing the nanosensor, such as transdermal application through one or more microneedles.

Once in the transdermal or other physiological environment, the conditions in the environment (e.g., the temperature, the pH, the presence of a certain ion, protein, small molecule, or other species) can cause the polymer to change from the fluid form to the rigid form. When the polymer changes from the fluid form to the rigid form, the nanosensor may remain within the polymer. Beneficially, the nanosensor disposed in the rigid polymer may be substantially immobilized within the polymer, so as not to move into the surrounding tissue or fluids. With this immobilization, the nanosensor may stay at a particular location in the intradermal or other physiological environment for a desired detection period (e.g., minutes, hours, days, or weeks) during which the nanosensor's interaction with a specific analyte can be detected.

In some embodiments, the polymer may be biocompatible and/or biodegradable.

In some embodiments, the polymer includes saccharide-derived units. The polymer may be a polysaccharide, such as, for example, alginic acid.

In some embodiments, the polymer includes disaccharide-derived units. For example, the polymer can include units derived from D-glucuronic acid and D-N-acetylglucosamine. In certain embodiments, the polymer can be hyaluronic acid.

In some embodiments, the polymer can be a copolymer of (meth)acrylate-derived units. The copolymer can include first (meth)acrylate-derived units and second (meth)acrylate-derived units. The first (meth)acrylate-derived units may include a hydrophilic side chain, and the second (meth)acrylate-derived units may include a hydrophobic side chain. Various conformations and compositions of the side chains of the first and second (meth)acrylate-derived units can be used to adjust the properties of the copolymer as desired, which include hydrophilicity, permeability and the ability to dispose or substantially immobilize a nanosensor.

In some embodiments, the side chains of the first (meth)acrylate-derived units may be hydrophilic, and can be water soluble or soluble in a water-miscible solvent, such as an alcohol. The side chains can have one or more heteroatoms, for example, nitrogen, oxygen or sulfur atoms. In some embodiments, the side chains have one or more hydroxy, thiol or amine groups.

In some embodiments, the side chains of the (meth) acrylate-derived units include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the side chains is a block copolymer including blocks of two or three different poly(alkylene oxide) polymers.

In some embodiments, the first (meth)acrylate-derived units can have the structure of formula (I):

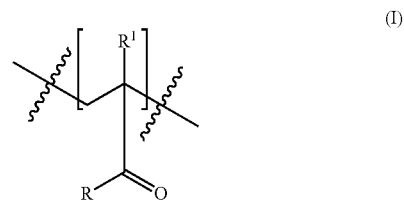

where R is a hydrophilic group and $R^1$ is hydrogen or methyl. In certain embodiments, the hydrophilic group includes one or more hydroxy groups, such as an alcohol. In some embodiments, $R^1$ is hydrogen. In some embodiments, $R^1$ is methyl.

In some embodiments, the first (meth)acrylate-derived units can have the structure of formula (Ia):

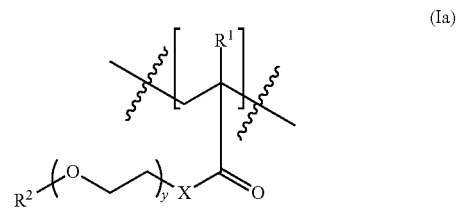

where X is —O—, —NR'— or —S—, y is an average value of from about 2 to about 250, $R^1$ is hydrogen or methyl, and $R^2$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR', where R' is —$C_1$-$C_{12}$alkyl. In some embodiments, $R^1$ is hydrogen. In some embodiments, $R^1$ is methyl.

In some embodiments, the first (meth)acrylate-derived units can have the structure of formula (Ia), where X and $R^2$ are as described above and y is such that the poly(ethylene glycol) has a number average molecular weight ($M_n$) of about 100 to about 10,000. In certain embodiments, y is selected so that the $M_n$ of the poly(ethylene glycol) falls within a range in Table 1.

TABLE 1

$M_n$ range of poly(ethylene glycol) in the first (meth) acrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |

TABLE 1-continued $M_n$ range of poly(ethylene glycol) in the first (meth) acrylate-derived units (values are approximate).

| Low | High |
| --- | --- |
| 4,000 | 5,000 |
| Low | High |
| 5,000 | 6,000 |
| 7,000 | 8,000 |
| 8,000 | 9,000 |
| 9,000 | 10,000 |

In certain embodiments, the copolymer has first (meth) acrylate-derived units having the structure of formula (Ia), where X is —O—, $R^2$ is methyl and y is such that the poly(ethylene glycol) has a number average molecular weight ($M_n$) of about 500.

In some embodiments, the second (meth)acrylate-derived units can have the structure of formula (II):

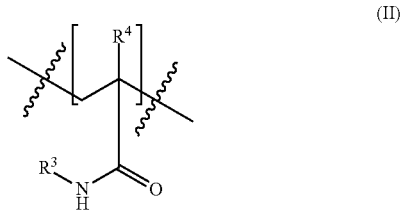

(II)

where $R^3$ is a hydrophobic group, and $R^4$ is hydrogen or methyl.

In some embodiments, the second (meth)acrylate-derived units have the structure of formula (II) where $R^3$ is —$C_1$-$C_{12}$alkyl, -cycloalkyl, or aryl. In certain embodiments, —$C_1$-$C_{12}$alkyl may be methyl, ethyl, propyl, isopropyl or butyl. In some embodiments, $R^4$ is hydrogen. In some embodiments, $R^4$ is methyl. In certain embodiments, -cycloalkyl may be -cyclopentyl or cyclohexyl. In certain embodiments, aryl may be phenyl. In certain embodiments, the second (meth)acrylate-derived units are derived from N-isopropylacrylamide.

In some embodiments, the polymer includes crosslinks. The crosslinks may be hydrophilic. For example, the crosslinks may include poly(ethylene glycol) units.

In embodiments where the polymer includes saccharide- or disaccharide-derived units, a portion of the saccharide- or disaccharide-derived units are thiolated and therefore capable reacting with a crosslinking agent to form crosslinks between different polymer chains. In some embodiments, the thiolated derivatives includes a covalently-bound thiol group, optionally through a linker. Crosslinking agents include those known in the art capable for covalent bond formation with a thiol group. For example, the crosslinking agent can be a di(meth)acrylate, such as poly(ethylene glycol) di(meth)acrylate, or a diepoxide, such as poly(ethylene glycol) diglycidyl ether.

In embodiments where the polymer includes (meth)acrylate-derived units, the copolymer can further include third (meth)acrylate-derived units with hydrophilic side chains covalently bound to third (meth)acrylate-derived units in different backbone chains of the copolymer (i.e., crosslinks). For example, the third (meth)acrylate-derived units can be derived from a di(meth)acrylate, such as poly(ethylene glycol) diacrylate or poly(ethylene glycol) dimethacrylate.

In some embodiments, the polymer can be configured to provide a porous network. The structure of the porous network includes regions within the polymer that are not occupied by polymer, these regions are referred to herein as "pores". The porous network of the polymer can facilitate interaction between the analyte (e.g., glucose) and the nanosensor disposed in the polymer.

The hydrophilic properties of the first (meth)acrylate-derived units can be varied to produce desired properties of the porous network, such as permeability of the analyte. For example, interaction of the nanosensor with the analyte can be dependent on the specific analyte being monitored, and thus, the porous network can be altered to obtain properties for monitoring a specific analyte. In some applications, the hydrophilicity of the porous network can be adjusted by changing the number alkylene oxide units in the side chain of the first (meth)acrylate-derived units. Similarly, the hydrophilicity of the porous network can be adjusted by modifying the number of carbon atoms (i.e., —C—, —CH—, —$CH_2$— or —$CH_3$) in the side chain of the second (meth)acrylate-derived units.

The hydrophilic properties of the porous network can also be adjusted by varying the ratio of the first and second (meth)acrylate-derived units in the copolymer backbone. The hydrophilicity of the porous network can be adjusted by changing the ratio of hydrophilic first (meth)acrylate-derived units to the hydrophobic second (meth)acrylate-derived units. For example, the copolymer may include a ratio of about 90 to 10 of first to second (meth)acrylate-derived units. In some examples, the ration is about 50:50, about 60:40, about 70:30 or about 80:20.

In some embodiments, the nanosensor is embedded within the polymer, i.e., surrounded by the polymer, in a physiological environment. The embedded nanosensor may be immobilized, so as to stay at a particular location in the physiological environment for a desired detection period (e.g., minutes, hours, days, or weeks), during which the nanosensor and can interact with a corresponding analyte of interest.

The nanosensor can be selected to monitor physiological levels of a specific analyte. For example, $Na^+$, $K^+$, $Ca^{2+}$, glucose, urea, creatinine, bicarbonate and chloride can be found in body fluids, including, for example, interstitial fluid, and can be indicative of medical conditions that can benefit from continuous or semi-continuous measurement.

In some examples, the polymer can include one or more ionophores that selectively interact with an ion. The ionophores could be covalently bound to the polymer backbone, for example, to the first or second (meth)acrylate-derived units. The ionophore may be selected to detect a specific ion. For example, an ionophore including one or more of valinomycin, bis[(benzo-15-crown-4)-4'-ylmethyl]pimelate), 2-dodecyl-2-methyl-1,3-propanediyl-bis-[N-(5'-nitro (benzo-15-crown-5)-4'-yl)carbamate], and 4-tert-butyl-2,2, 14,14-tetrahomo-4a,14a-dioxacalix[4]arene-tetraacetic acid tetra-tert-butyl ester may be used to detect potassium.

In some embodiments, the polymer and the nanosensor may be selected to allow for the detection a specific analyte. For example, the polymer can include an ionophore that is sensitive to $Na^+$ and the nanosensor can include a pH-sensitive fluorophore. When $Na^+$ enters the ionophore, a proton is displaced, thereby changing the pH and the response of the pH-sensitive fluorophore.

In another aspect, a method for making the composition is disclosed. The method can involve:

a) forming a mixture comprising nanosensors and a polymer, where the nanosensors include nanoparticles having a detectable label and configured to interact with a specific analyte present in a transdermal environment; and b) subjecting the mixture to conditions suitable for curing the polymer to provide a nanosensor-containing polymer in a fluid form.

In some embodiments of the method, the method involves:

a) forming a mixture comprising nanosensors and a polymer, where the nanosensors include nanoparticles having a detectable label and configured to interact with a specific analyte present in a transdermal environment;

b) subjecting the mixture to conditions suitable for curing the polymer to provide a nanosensor-containing polymer in a fluid form; and c) subjecting the resulting polymer to a temperature above its lower critical solution temperature to provide a nanosensor-containing polymer in a rigid form.

In some embodiments of the method, the nanosensor and polymer are selected to provide the composition described above.

In some embodiments of the method, the polymer is a copolymer and the method can involve:

a) forming a mixture including nanosensors, a first monomer, a second monomer and an initiator, where the nanosensors include nanoparticles having a detectable label and configured to interact with a specific analyte present in a transdermal environment; and b) subjecting the mixture to conditions suitable for copolymerizing the first monomer and second monomer to provide a nanosensor-containing copolymer in a fluid form.

In some embodiments of the method, the method can involve:

a) forming a mixture including nanosensors, a first monomer, a second monomer and an initiator, where the nanosensors include nanoparticles having a detectable label and configured to interact with a specific analyte present in a transdermal environment;

b) subjecting the mixture to conditions suitable for copolymerizing the first monomer and second monomer to provide a nanosensor-containing copolymer in a fluid form; and c) subjecting the resulting copolymer to a temperature above its lower critical solution temperature to provide a nanosensor-containing copolymer in rigid form.

In some embodiments of the method, the nanosensor, first monomer and second monomer are selected to provide the composition described above.

In some embodiments, the first and second monomers are (meth)acrylate monomers. The ratio of the components in the mixture can vary depending on the desired properties of the resulting composition. For example, adjusting the amount of the first (meth)acrylate monomer having a second hydrophilic side chain can alter the porous network of the crosslinked, hydrophilic copolymer. Controlling the properties of the porous network can allow for the tuning of the permeability of the network.

The mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino) succinic acid, or phosphate buffered saline (PBS). In some embodiments, the mixture can be formed in a mixture of a buffered aqueous solution and ethanol.

The first and second (meth)acrylate monomers include hydrophilic side chains that can have one or more heteroatoms. The first and second side chains can include one or more alkylene oxide units to form the crosslinked, hydrophilic copolymer described herein.

In some embodiments of the method, the first (meth)acrylate monomer has the structure of formula (III):

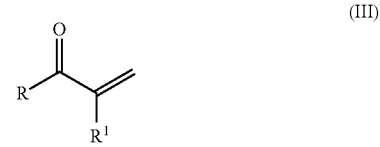

where R and $R^1$ are selected to provide the first (meth)acrylate-derived monomeric unit of the crosslinked, hydrophilic copolymer described herein.

In some embodiments of the method, the first (meth)acrylate monomer has the structure of formula (IIIa):

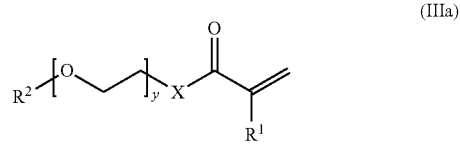

where X, y, $R^1$, $R^2$ and R' are selected to provide the first (meth)acrylate-derived monomeric unit of the crosslinked, hydrophilic copolymer described herein. In certain embodiments, the first (meth)acrylate monomer is poly(ethylene glycol) methacrylate.

In some embodiments of the method, the second (meth)acrylate monomer has the structure of formula (IV):

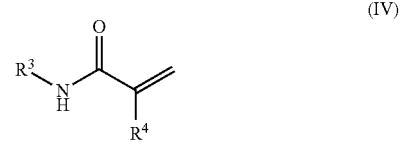

where $R^3$ and $R^4$ are selected to provide the second (meth)acrylate-derived monomeric unit of the crosslinked, hydrophilic copolymer described herein.

In some embodiments, the second (meth)acrylate monomer have the structure of formula (II) where $R^3$ is —$C_1$-$C_{12}$alkyl, -cycloalkyl, or aryl. In some embodiments, $R^4$ is hydrogen. In some embodiments, $R^4$ is methyl. In certain embodiments, —$C_1$-$C_{12}$alkyl may be methyl, ethyl, propyl, isopropyl or butyl. In certain embodiments, -cycloalkyl may be -cyclopentyl or -cyclohexyl. In certain embodiments, aryl may be phenyl. In certain embodiments, the second (meth)acrylate monomer is N-isopropylacrylamide.

In some embodiments, the mixture further includes a crosslinking agent. In embodiments where the polymer chains are saccharide or disaccharide derived, the crosslinking agent may be capable of forming a covalent bond with a thiol group of a thiolated polymer backbone.

In embodiments where the polymer is a copolymer, the crosslinking agent can be a molecule having two terminal (meth)acrylate groups tethered by a hydrophilic linker (i.e., a di(meth)acrylate monomer). The hydrophilic linker is selected to provide the crosslinks between third (meth)acrylate-derived units in different backbone chains of the crosslinked, hydrophilic copolymer described herein. The extent of crosslinking in crosslinked, hydrophilic copolymer can be controlled by adjusting the amount of di(meth)acrylate monomer in the mixture.

Conditions suitable to initiate polymerization (i.e., curing) can be selected based on the characteristics of the initiator and the monomers being polymerized, and as so not to degrade the nanosensor. The temperature and pH of the method can be selected to preserve the nanosensor. In certain embodiments the initiator is activated with ultraviolet (UV) light. For example, when 2,2-diemthoxy-2-phenylacetophenone is used as an initiator, curing can be performed with UV light. In some embodiments, the initiator is ammonium persulfate "APS" and tetramethylethylenediamine (TEMED), optionally including riboflavin or riboflavin-5'-phosphate.

In some embodiments of the method, the fluid polymer (or copolymer) may be subjected to an environment capable of promoting phase transformation to provide a rigid nanosensor-embedded polymer matrix. Phase transformation may occur above the composition's lower critical solution temperature, which may be dependent on the composition of the polymer matrix. For example, a fluid copolymer of N-isopropylacrylamide and poly(ethylene glycol) methacrylate may undergo phase transformation to a rigid copolymer at physiological temperature. Thus, subjecting a fluid copolymer including a nanosensor to an intradermal environment would result in a rigid nanosensor-embedded copolymer matrix. The composition of the polymer can be modified to adjust the lower critical solution temperature of the polymer for the desired application.

In some embodiments, the fluid polymer is introduced to an intradermal environment through transdermal delivery. Many transdermal delivery techniques and devices are known in the art, such as patches, microneedles, and microneedle arrays. In certain examples, the fluid polymer composition is introduced to the intradermal environment through a microneedle or microneedle array.

As referred to above, "(meth)acrylate" means the polymeric unit or monomer is acrylate (i.e., —OC(O)C(CH$_3$)C=CH$_2$) or methacrylate (i.e., —OC(O)C(H)C=CH$_2$). Although the crosslinked, hydrophilic copolymers in the above disclosure include (meth)acrylate groups, there are a number of ethylenically unsaturated groups known in the art to be capable of undergoing polymerization. Ethylenically unsaturated monomers and macromers may be either acrylic- or vinyl-containing. Vinyl-containing monomers contain the vinyl grouping (CH$_2$=CH—), and are generally highly reactive. Acrylic-containing monomers are represented by the formula:

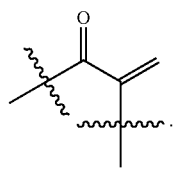 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A composition, comprising:
   a nanosensor comprising a nanoparticle having a detectable label, wherein the nanosensor is configured to interact with a specific analyte in an intradermal environment; and
   a polymer comprising first monomer-derived units and second monomer-derived units, wherein
   the first monomer-derived units have the structure of formula (Ia):

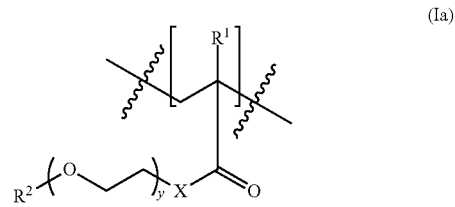

wherein
X is —O— or —S—;
y is 0-10;
R$^1$ is hydrogen or methyl; and
R$^2$ is hydrogen, —C$_1$-C$_{12}$alkyl, —C$_1$-C$_{12}$alkyl-OH, —SiR'$_3$, —C(O)—C$_1$-C$_{12}$alkyl, —C$_1$-C$_{12}$alkyl-C(O)OR', wherein R' is —C$_1$-C$_{12}$alkyl, the second monomer-derived units have the structure of formula (II):

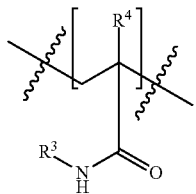
(II)

wherein
R³ is a hydrophobic group; and
R⁴ is hydrogen or methyl,
wherein the polymer is configured to change from a fluid form to a rigid form in response to a temperature increase;
wherein the nanosensor is disposed in the polymer.

2. The composition of claim 1, wherein the temperature increase can be achieved by transdermal application into the intradermal environment.

3. The composition of claim 1, wherein the first monomer-derived units are derived from poly(ethylene glycol) methyl ether methacrylate.

4. The composition of claim 1, wherein $R^3$ is —$C_1$-$C_{12}$alkyl, cycloalkyl, or aryl.

5. The composition of claim 1, wherein the second monomer-derived units are derived from N-isopropylacrylamide.

6. The composition of claim 1, wherein the detectable label comprises a fluorophore.

7. The composition of claim 1, wherein the ratio of the first monomer-derived units and second monomer-derived units in the copolymer is about 90:10.

8. The composition of claim 1, wherein the ratio of the first monomer-derived units and second monomer-derived units in the copolymer is about 80:20.

9. The composition of claim 1, wherein the ratio of the first monomer-derived units and second monomer-derived units in the copolymer is about 70:30.

10. The composition of claim 1, wherein the ratio of the first monomer-derived units and second monomer-derived units in the copolymer is about 60:40.

11. The composition of claim 1, wherein the ratio of the first monomer-derived units and second monomer-derived units in the copolymer is about 50:50.

* * * * *